(12) United States Patent
Ling

(10) Patent No.: US 8,128,459 B2
(45) Date of Patent: *Mar. 6, 2012

(54) POLISHING HOLDER FOR WORKPIECE END SURFACE

(76) Inventor: Kow-Je Ling, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 12/149,593

(22) Filed: May 5, 2008

(65) Prior Publication Data
US 2010/0233946 A1    Sep. 16, 2010

(30) Foreign Application Priority Data

May 22, 2007    (TW) ............................... 96118171 A

(51) Int. Cl.
*B24B 49/00* (2006.01)
(52) U.S. Cl. .......... 451/11; 451/271; 451/278; 451/384; 451/390
(58) Field of Classification Search ................ 451/9, 10, 451/11, 41, 57, 256, 270, 271, 278, 283, 451/285, 384, 390
See application file for complete search history.

(56) References Cited

U.S. PATENT DOCUMENTS

| | | | | |
|---|---|---|---|---|
| 5,038,524 A | * | 8/1991 | Moulin | 451/548 |
| 5,216,846 A | * | 6/1993 | Takahashi | 451/57 |
| 5,351,445 A | * | 10/1994 | Takahashi | 451/271 |
| 5,547,418 A | * | 8/1996 | Takahashi | 451/278 |
| 6,039,630 A | * | 3/2000 | Chandler et al. | 451/6 |
| 6,077,154 A | * | 6/2000 | Takashi et al. | 451/271 |
| 2004/0237331 A1 | * | 12/2004 | Sarfaty et al. | 34/218 |
| 2006/0035562 A1 | * | 2/2006 | Sarfati et al. | 451/5 |

* cited by examiner

*Primary Examiner* — Eileen P. Morgan

(57) ABSTRACT

A holder for workpieces with end surfaces thereof being polished comprises a main body and a framework in which the main body is provided with a plurality of fixtures for holding the workpieces and the ring-shaped first supporting portion, and the framework is provided with the second supporting portion surrounding the outer side of the first supporting portion. The second supporting portion limits the angular movement of the first supporting portion to enable the main body to keep parallel to the polishing surface during the end surface of the respective workpiece is brought into contact with the polishing surface. The structure of the holder is capable of reducing the fabrication time and cost of the first supporting portion tremendously.

10 Claims, 8 Drawing Sheets

POLISHING HOLDER FOR WORKPIECE END SURFACE

BACKGROUND OF THE INVENTION

1. Field of the Invention

The present invention relates to an apparatus for polishing an end surface of a workpiece, and, more particularly, to a holder for supporting a polished end surface of an optical fiber.

2. Description of Related Art

The optical fiber communication is an indispensable communication tool at present and it will be in the future. The main structure of an optical fiber connector used in the field of communication is constituted by an optical fiber 11 passing through a ferrule 12 and then being adhered to the ferrule 12 with an adhesive. The ferrule 12 can be made of plastic, glass or ceramics. The ferrule 12 has a spherical end surface 121 which projects outward and is pressed by an elastic polishing surface and worked with a process which includes coarse grinding, fine grinding and polishing. The finished spherical surface 121 must be worked as a flawless curved surface. An optical axis of the spherical surface 121 can be either parallel to a central line of the optical fiber 11 or inclining a small angle with the central line.

A conventional method for polishing an end surface of the optical fiber is to keep the end surface stationary and to rotate and revolve the polishing surface in the process of polishing the end surface. It can be known from a mathematical analysis disclosed in Taiwan Patent No. 485863 entitled as "Polishing apparatus for optical fiber end surface" that if the movement of the polishing surface is rotation plus revolution, the end surface of the optical fiber is merely arranged on the circumference of the holder, and if there is only revolution without rotation, the wearing degree of every spot on the whole end surface is the same. The end surfaces of a plurality of optical fibers can be equally arranged on the holder evenly. Besides, the reference mentioned above also discloses that if the polishing surface is fabricated to be strip-shaped, one side of the strip-shaped polishing surface is provided with coarse polishing particles and another side of the strip-shaped polishing surface is provided with fine polishing particles. FIG. 2 shows that several holders 2, 3 and 4 are on a strip-shaped polishing surface 5 with a right side 6 of the polishing surface being provided with coarse particles and a left side 7 of the polishing surface being provided with fine particles. The pressure between the end surface of the respective optical fiber of the holders and the polishing surface 5 can be uniform if an arrangement is performed properly. The holders 2, 3 and 4 are capable of sliding on the polishing surface 5 from the side with coarse particles toward the side with fine particles and hence, the process including the coarse grinding, the fine grinding and the polishing can be done sequentially. Thus, the problem of the pressure between the respective end surface and the polishing surface being not uniform can be solved, and, theoretically, the end surfaces of a great number of optical fibers can be polished simultaneously.

Basically, an uneven pressure is originated from the following reasons:

1. The supporting point of the holder is not on a plane of application of force generated from a friction between the end surface of the optical fiber and the polishing surface so that a torque is yielded to slant the holder so as to generate the uneven pressure.
2. The polishing surface not parallel to the holder may yield the uneven pressure too when the holder is fixedly clipped.

Please refer to FIGS. 3 and 4. The conventional apparatus for polishing the end surface of the optical fiber comprises a polishing surface 20, ferrule 22, a holder 23 and a pressing rod 24. An end surface 251, 252 of the respective optical fiber 25 is attached to the ferrule 22. When there is a relative movement between the end surface 251, 252 and the polishing surface 21, the holder 23 is subject to a transverse force at an end face thereof. But, the supporting point is at one of contact points 31, 32 right at this time such that the holder 23 is subject to a counterclockwise torque to slant the holder 23 as shown in FIG. 4 to cause the end surface 251 to be lower than the end surface 252, i.e., it causes the pressure acting on the end surface 251 is greater than on the end surface 252.

For solving the aforementioned problem, U.S. Pat. No. 5,216,846 discloses a spacer for maintaining a constant distance between the workpiece and the polishing surface. Because the polishing surface is elastic, maintaining the constant distance means maintaining a uniform pressure. In such a manner, part of the uneven pressure is borne by the spacer to overcome the preceding problem to some extent, but, the torque is still there because the original structure is kept without change such that the unfavorable factor resulting in the uneven pressure is still there. Moreover, U.S. Pat. No. 6,039,630 discloses a pressure sensor is utilized to measure the pressure instantly and compensate the unevenness of pressure by means of a method with an electronically controlling spring.

Furthermore, U.S. Pat. No. 6,077,154 and U.S. Pat. No. 5,351,445 respectively teach a design for clipping and fixing an end surface of an optical fiber as shown in FIG. 5 in which holder 41 is provided with a plurality of optical fiber fixtures 42 for clipping optical fibers 43. The holder 41 is fixed by the fixtures 42 on the upper side of the polishing surface 45. Because the holder 41 is clipped and fixed, the problem of slanting generated from the torque basically does not happen. But, there is still another problem which has to be solved; because the holder 41 is clipped and fixed, and the direction to which the polishing surface 45 faces is also fixed, the holder 41 and the polishing surface 45 are not able to be accurately parallel to each other. In order to overcome the deficiency, the common practice is to adjust the fixtures 42 angularly for fixing the holder 41. But, this is not a natural contact such that the holder 41 is always a little unparallel to the polishing surface 45. Besides, the pressure between the end surface of the optical fiber 43 and the polishing surface is produced by a force exerting upwards from the bottom, and it is not only too complicated but also not suitable for automation. Furthermore, if the polishing surface is strip as shown in FIG. 2 for being slid with several holders simultaneously, it is then difficult for the end surface on each holder to keep the uniform pressure.

Two principles for end surfaces of optical fibers disposed at different positions on a holder capable of being subjected to a uniform pressure are described in the following:

1. The holder shouldn't be clipped and fixed, and must be naturally contact with the polishing surface in case of the polishing surface is hard and inelastic. That is, the holder oscillates up and down with oscillation of the polishing surface, and the average pressure acting on the end surface at different positions on the holder keeps uniform when the holder oscillates up and down. The holder and the polishing surface must be kept fairly parallel to each other, and in the meantime, the polishing surface is capable of being pressed if the polishing surface is elastic.
2. A plane formed by the end surface in the process of polishing is a plane of application of force that is a plane constituted by a force exerted to the holder by the polishing surface. It is necessary to provide one or several supporting points for the holders because, in principle, the holder does not move or rotate with the polishing surface in the process of polishing. In order to obtain the uniform pressure, these supporting points must be on the plane of application of force to keep the holder from moving or rotating with the polishing surface.

Please refer to FIG. 6. U.S. Pat. No. 7,063,062 discloses that a plurality of symmetrical accepting grooves 61 for receiving counterweights 62 are disposed on the periphery of a main body 60 of a holder; in this way, the main body 60 allows the end surfaces of a plurality of optical fibers 63 to have down pressing forces exerting on a polishing surface 64 such that the main body 60 contacts naturally with the polishing surface 64. A plurality of symmetrical fixing rods 65 are disposed at the sides of the main body 60, a contact portion 651 is disposed on the bottom of each fixing rod 65 and positioned in a fixing groove 661 of each framework 66. A weephole 662 for draining fluid dropping into the accepting grooves 661 during polishing. A contact surface between the contact portion 651 and the fixing groove 661 is the same as a contact surface between the bottoms of the optical fibers 63 and the polishing surface 64 to allow the supporting points of the main body 60 to be on a plane of application of force generated by the bottoms of the optical fibers 63 and the polishing surface 64. Thus, a torque is not yielded to slant the main body 60 and a phenomenon of generating the uneven pressure can be avoided.

The symmetrical fixing rods 65 of the holder shown in FIG. 6 fix the main body 60 such that the main body 60 is incapable of rotating. Only a portion of the polishing surface 64, which contacts with the end surface of the optical fiber, is used instead of all polishing points of the polishing surface 64 being used uniformly. Besides, bottom ends of the four fixing rods 65 of the main body 60 must be kept at the same plane, and it is a very difficult manufacturing process.

U.S. patent application Ser. No. 11/812,967 discloses a holder for supporting an end surface of an optical fiber during polishing. A main body and a framework of the holder are respectively provided with corresponding fixing portions, at least one of the two fixing portions is provided with at least one set of upper and lower contact portions, the upper contact portion and the lower contact portion on each set are respectively disposed at the upper side and the lower side of a contact plane between the end surface of the workpiece and a polishing surface. Restriction to mutual contacts between the upper contact portion, the lower contact portion and another fixing portion is utilized for the main body being capable of maintaining parallel to the polishing surface so as to enhance the polishing speed and quality.

SUMMARY OF THE INVENTION

For further improving the supporting structure between a main body and a framework of a holder such that the supporting structure is capable of being manufactured more easily to save the production time and cost; besides, a position of the main body corresponding to the polishing surface can be changed in the process of polishing such that each polishing point of the polishing surface is uniformly applied for promoting the polishing quality.

The main object of the present invention is to provide a holder for an end surface of a workpiece during polishing for the supporting structure between the main body and the framework to be manufactured more easily.

Another object of the present invention is to provide a holder for an end surface of a workpiece for an end surface of an optical fiber on the main body to be uniformly brought into contact with the polishing surface; each polishing point of the polishing surface can be uniformly worn out for the end surface of the optical fiber obtaining a uniform wearing degree and enhancing the yield rate during the end surface of the optical fiber being polished.

Still another object of the present invention is to provide a holder for an end surface of a workpiece for the optical fiber to be arranged and held more conveniently while the end surface thereof is polished.

For attaining to the objects mentioned above, the present invention proposes a holder for an end surface of a workpiece comprises:

a main body which combines a plurality of fixtures for respectively holding polished workpieces, and is provided with a ring-shaped first supporting portion at the periphery thereof; and a framework which is provided with a second supporting portion surrounding the outer side of the first supporting portion;

whereby, the second supporting portion limits an angular movement of the first supporting portion to enable the main body to keep parallel to a polishing surface during an end surface of the workpiece being brought into contact with the polishing surface.

BRIEF DESCRIPTION OF THE DRAWINGS

The present invention can be more fully understood by reference to the following description and accompanying drawings, in which.

DETAILED DESCRIPTION OF THE PREFERRED EMBODIMENTS

Figure 7:
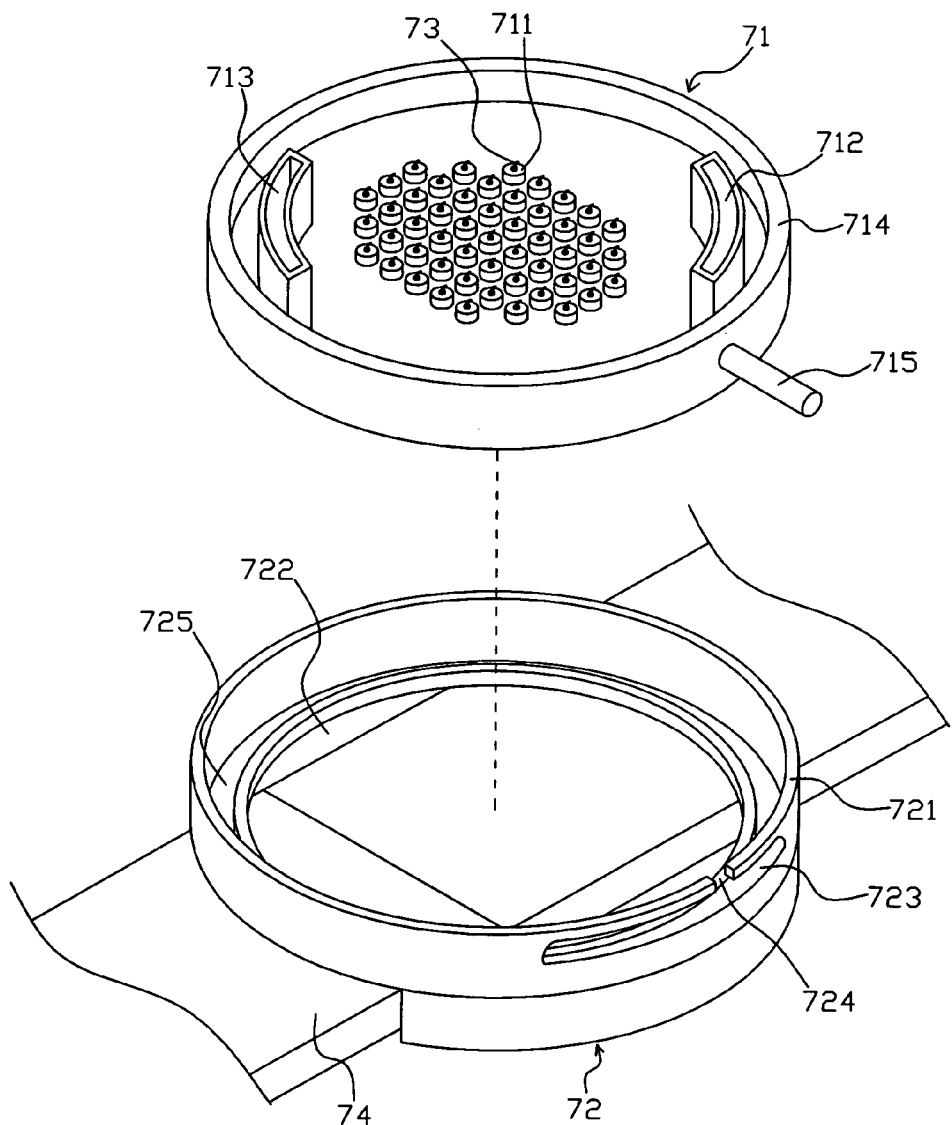
FIG. 7 is an exploded view of the first preferred embodiment of a polishing apparatus according to the present invention.
Figure 8:
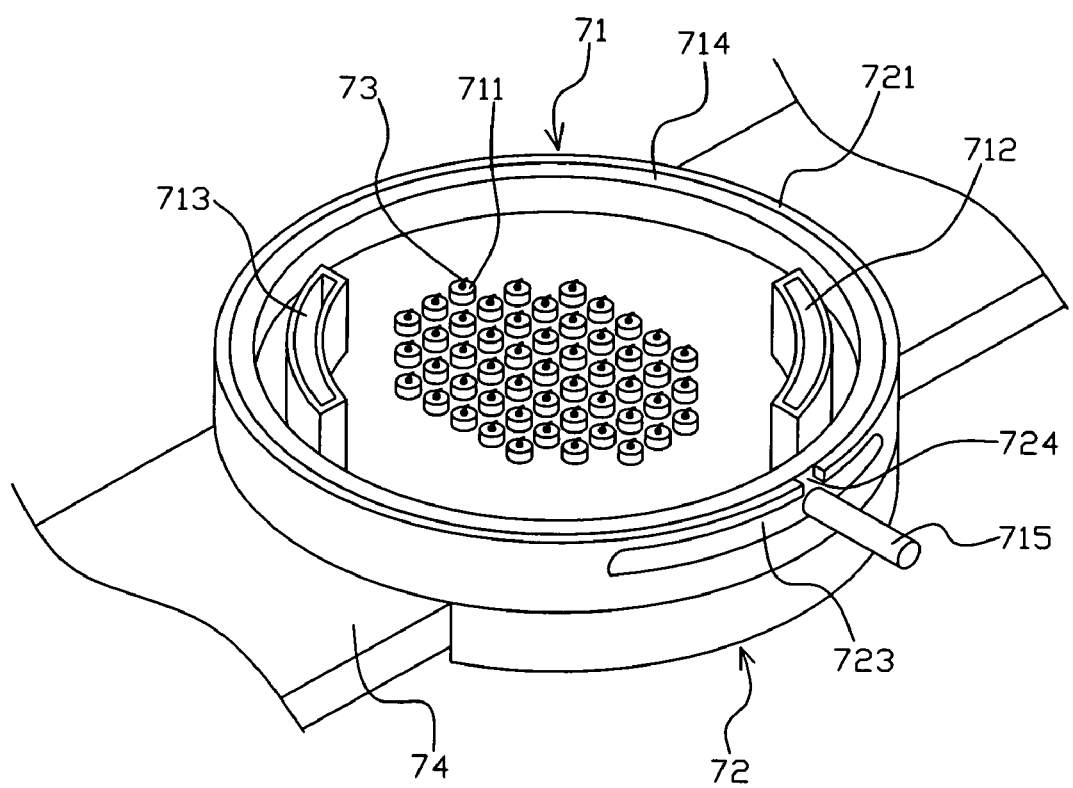
FIG. 8 is an assembled perspective view of the first preferred embodiment of a polishing apparatus according to the present invention.

Please refer to FIGS. 7 and 8. The first preferred embodiment of a holder according to the present invention comprises a main body 71 and a framework 72. The main body 71 is provided with a plurality of fixtures 711; each fixture 711 at least has one ferrule to be joined to an optical fiber 73. The main body 71 is further provided with a plurality of accepting grooves 712, 713 close to the periphery thereof to receive counterweights for exerting a downward pressing force on the main body 71. But, if there is no counterweight added to exert the downward pressing force on the main body 71, a rotational speed of the polishing surface may be controlled by a friction force between the polishing surface and end surfaces of the optical fibers, a rotational speed of the polishing surface must be far smaller than a revolutionary speed thereof. The accepting grooves 712, 713 respectively can be curve-shaped grooves, cylindrical grooves or elongated grooves. A periphery of the main body 71 is provided with a ring-shaped first supporting portion 714, and the outer wall of the first supporting portion 714 is disposed with at least one poker bar 715. The framework 72 contains the main body 71 and has a ring-shaped second supporting portion 721 surrounding the outer side of the first supporting portion 714. A continuous type polishing surface 74 is disposed inside and passes through the bottom of the second supporting portion 721. A middle part of the framework 72 is provided with a through hole 722 for the end surfaces of the optical fibers 73 to be pressed against the polishing surface 74 for the polishing operation to be processed. The second supporting portion 721 is provided with a long slot 723 and a breach 724 communicating with the long slot 723 for the poker bar 715 to pass through the breach 724 and be located in the long slot 723 as shown in FIG. 8.

The inner side of the second supporting portion 721 is provided with a ring-shaped retaining groove 725. The bottom of the first supporting portion 714 is received in the retaining groove 725 such that the main body 71 is capable of keeping parallel to the polishing surface 74 in the process of polishing by designing a contact plane of the first supporting portion 714 with the retaining groove 725 to be approximately the same as a contact plane of the end surface of the respective optical fiber 73 with the polishing surface 74. Furthermore, contact positions of the end surfaces of the optical fibers 72 on the polishing surface 74 may be changed by pushing the poker bar 715 to rotate the main body 71 an angular movement relative to the framework 72 and the polishing surface 74 to allow all polishing points of the polishing surface 74 to be brought into contact with the end surface of the optical fiber 73 uniformly such that each polishing point of the polishing surface 74 can be applied evenly with wearing degree thereof being uniform, and to allow multiple optical fibers 73 which are distributed at different positions can be polished identically to enhance the yield rate during the end surfaces of the optical fibers 73 being polished.

Figure 1:
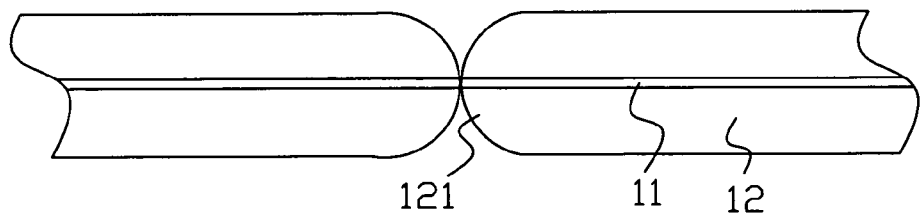
FIG. 1 is a schematic view of the conventional optical fiber connector.
Figure 2:
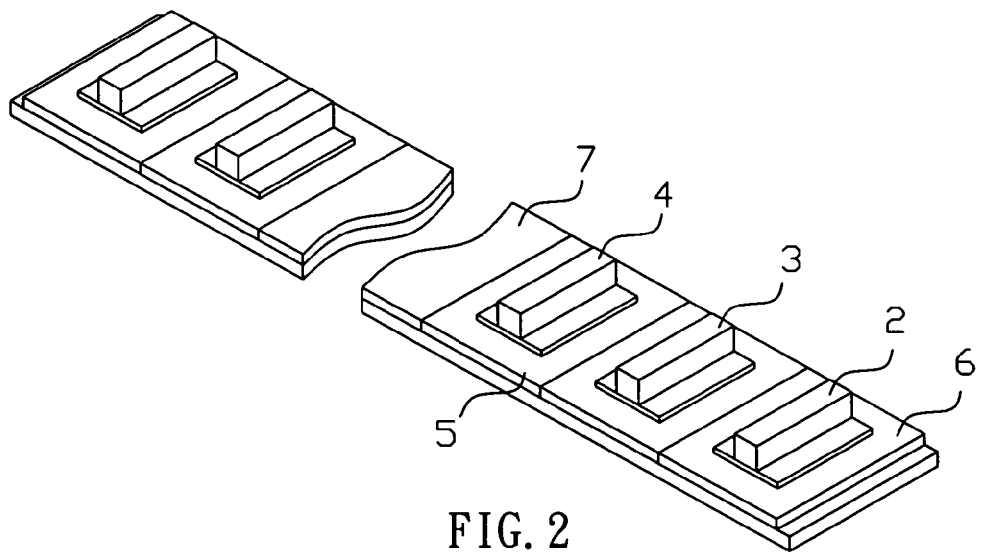
FIG. 2 is a fragmentary perspective view of the conventional polishing apparatus.
Figure 3:
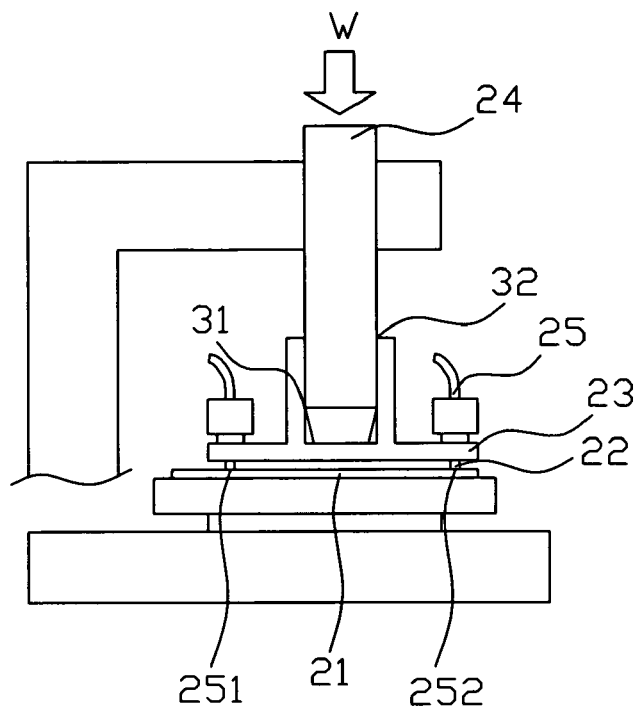
FIG. 3 is a fragmentary plan view of the conventional polishing apparatus.
Figure 4:
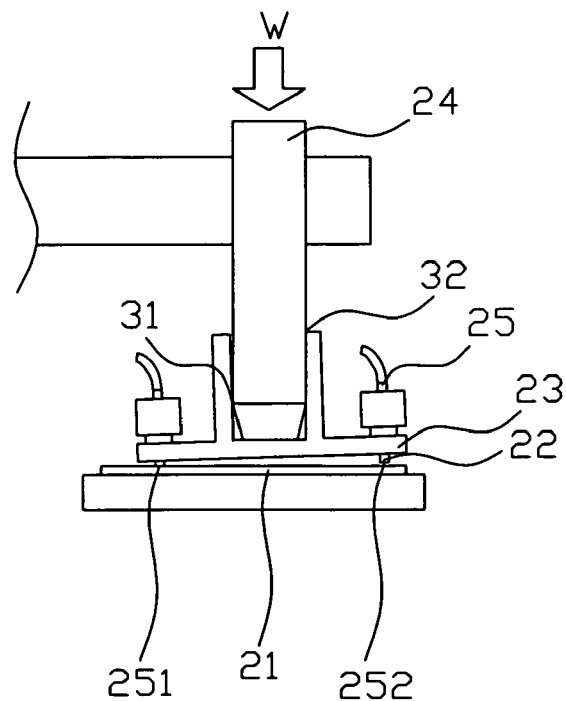
FIG. 4 is a fragmentary plan view of the conventional polishing apparatus in use.
Figure 5:
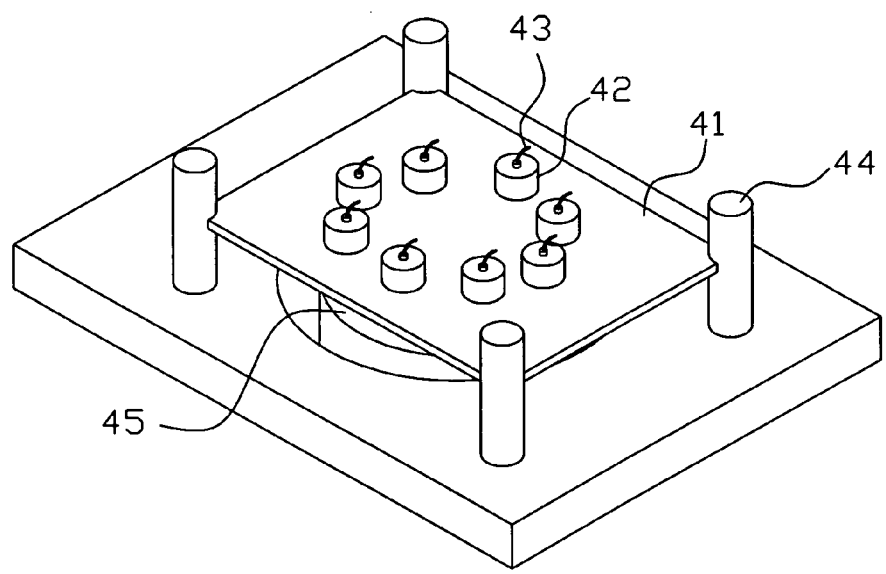
FIG. 5 is a perspective view of the conventional holder in association with fixtures.
Figure 6:
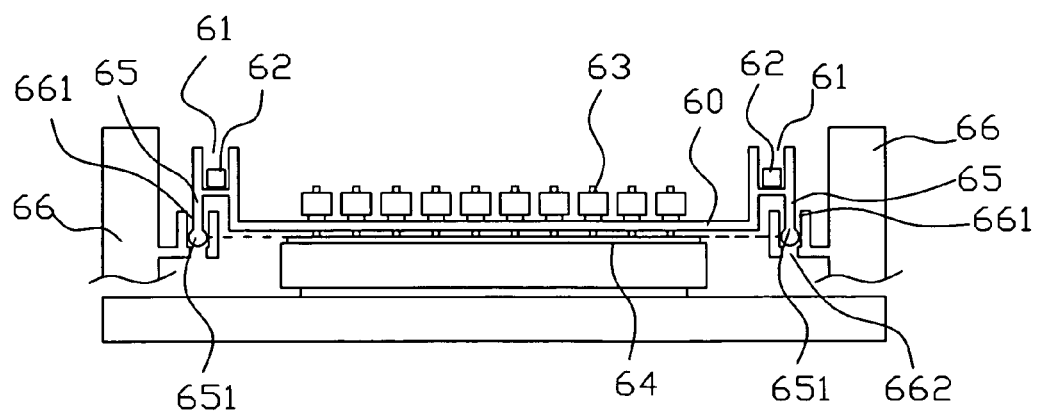
FIG. 6 is a fragmentary plan view of the conventional holder.

The supporting structure for the main body 71 and the framework 72 is constituted by the first and second supporting portions 714, 721 and the retaining groove 725. It is unnecessary to process a difficult operation for adjusting the bottom ends of the four fixing rods 65 to be at the same level as shown in FIG. 6 while the first supporting portion 714 being manufactured such that the production time and cost can be reduced tremendously.

Figure 9:
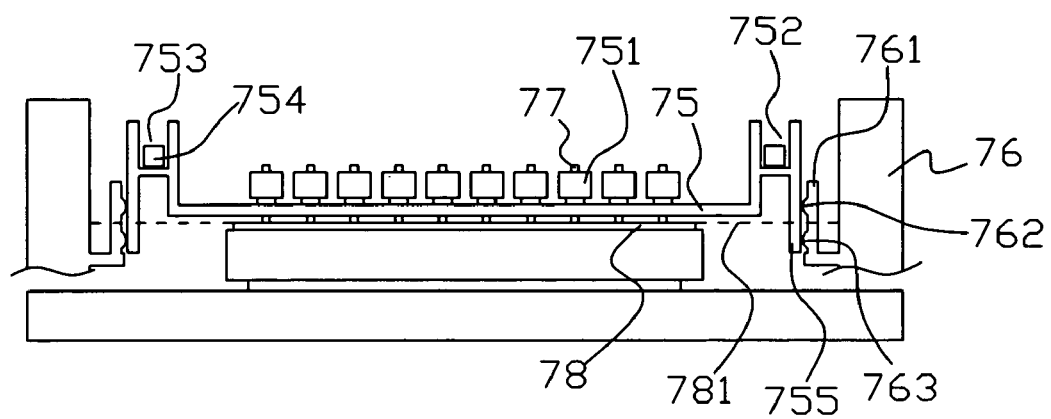
FIG. 9 is a fragmentary plan view of the second preferred embodiment of a polishing apparatus according to the present invention.

Please refer to FIG. 9. The second preferred embodiment of the holder according to the present invention comprises a main body 75 and a framework 76. The main body 75 is provided with a plurality of fixtures 751; each fixture 751 is attached with at least one ferrule to couple to an optical fiber 77. The main body 75 has a plurality of symmetrical accepting grooves 752, 753 next to the periphery thereof for receiving counterweights 754. The periphery of the main body 75 is provided with a ring-shaped first supporting portion 755. The framework 76 is provided with a ring-shaped second supporting portion 761. The second supporting portion 761 surrounds the outer side of the first supporting portion 755. A polishing surface 78 is further disposed inside the second supporting portion 761. A middle part of the framework 76 is provided with a through hole for the end surface of the optical fiber 77 to be pressed against the polishing surface 78 to process a polishing operation. An outer wall of the first supporting portion 755 is disposed with at least one poker bar, and the second supporting portion 761 is provided with a long slot for accepting the poker bar and a breach communicating with the long slot for the poker bar to pass through the breach and to be located in the long slot as the structure described in the first embodiment although it is not shown in FIG. 9. An inner wall of the second supporting portion 761 is provided with projecting outward upper and lower contact portions 762, 763. The upper and lower contact portions 762, 763 are respectively positioned in a range of approximately 2 centimeters above and below a contact plane 781 between the polished end surface of the optical fiber 77 and the polishing surface 78. The upper and lower contact portions 762, 763 can respectively limit a deviation range of the first supporting portion 755 in the process of polishing. The present embodiment also provides a supporting structure for the main body to be manufactured easily and enable each polishing point of the polishing surface to be worn out equally and the wearing degree of the end surface of the respective optical fiber to be uniform for enhancing the yield rate during the end surfaces of the optical fibers being polished.

Figure 10:
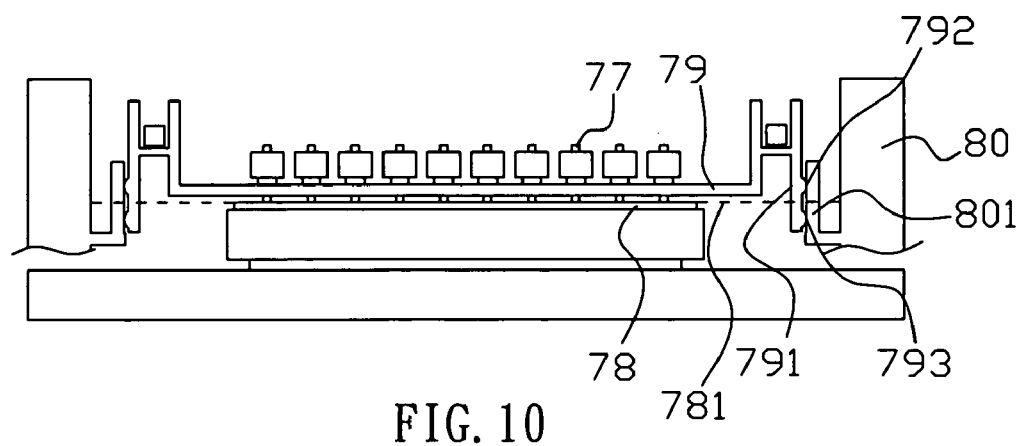
FIG. 10 is a fragmentary plan view of the third preferred embodiment of a polishing apparatus according to the present invention.

Please refer to FIG. 10 in company with FIG. 9. The third preferred embodiment of the holder according to the present invention comprises a main body 79 and a framework 80, a structure thereof is approximately the same as the second embodiment shown in FIG. 9. The difference of the present embodiment is in that an outer wall of the first supporting portion 791 of the main body 79 is provided with projecting outward upper and lower contact portions 792, 793 instead of the upper and lower contact portions 762, 763 of the second supporting portion 761 of the second embodiment. The upper and the lower contact portions 792, 793 are respectively positioned in a range approximately 2 centimeters above and below a contact plane 781 of the polished end surface of the optical fiber 77 with the polishing surface 78, and the second supporting portion 801 can respectively limit angular movements of the upper and lower contact portions 792, 793 of the first supporting portion 791. The present embodiment also provides a supporting structure for the main body to be manufactured easily and enable each polishing point of the polishing surface to be worn out equally and the wearing degree of the end surfaces of the optical fibers to be uniform for enhancing the yield rate during the end surfaces of the optical fibers being polished.

Figure 11:
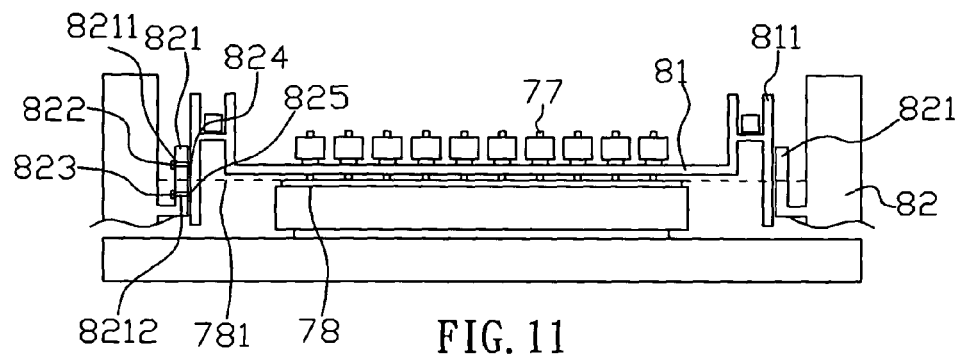
FIG. 11 is a fragmentary plan view of the fourth preferred embodiment of a polishing apparatus according to the present invention.

Please refer to FIG. 11 in company with FIG. 9. The fourth preferred embodiment of the holder according to the present invention comprises a main body 81 and a framework 82, and a structure thereof is approximately the same as the second embodiment shown in FIG. 9. The difference of the present embodiment is in that a second supporting portion 821 is provided with a plurality of symmetrically disposed screw holes 8211, 8212, and the screw holes 8211, 8212 are respectively engaged with screws 822, 823 projecting outward from an inner wall of the second supporting portion 821 to form the upper and lower contact portions 824, 825 instead of the upper and lower contact portions 762, 763 of the second supporting portion 761 of the second embodiment. The upper and lower contact portions 824, 825 are respectively positioned in a range approximately 2 centimeters above and below a contact plane 781 of the end surface of the respective optical fiber 77 with the polishing surface 78 to limit the angular movement of the first supporting portion 811. The present embodiment also provides a supporting structure for the main body to be manufactured easily and enable each polishing point of the polishing surface to be worn out equally and the wearing degree of each optical fiber end surface to be uniform for enhancing the yield rate during the end surfaces of the optical fiber being polished. Besides, spaces between the upper and lower contact portions 824, 825 and the first supporting portion 811 can be adjusted with the screws 822, 823.

Figure 12:
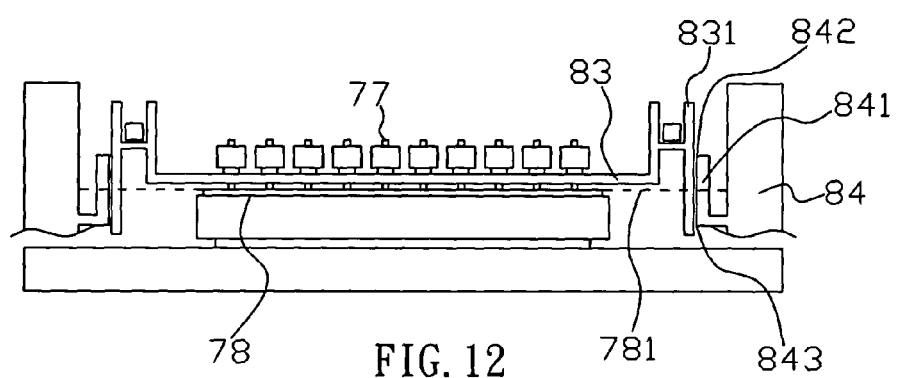
FIG. 12 is a fragmentary plan view the fifth preferred embodiment of a polishing apparatus according to the present invention.

Please refer to FIG. 12 in company with FIG. 9. The fifth preferred embodiment of the holder according to the present invention comprises a main body 83 and a framework 84, and a structure thereof is approximately the same as the second embodiment shown in FIG. 9. The difference of the present embodiment is in that the lower end of a first supporting portion 831 is lower than the lower end of a second supporting portion 841, and the upper and lower ends of an inner wall of the second supporting portion 841 are utilized to be upper and lower contact portions 842, 843 respectively instead of the upper and lower contact portions 762, 763 disposed on the second supporting portion 761 of the second embodiment. The upper and lower contact portions 842, 843 are respectively positioned in a range approximately 2 centimeters above and below a contact plane 781 of the end surface of the respective optical fiber 77 with the polishing surface 78 to limit the angular movement of the first supporting portion 831. The present embodiment also provides a supporting structure for the main body to be manufactured easily to enable each polishing point of the polishing surface to be worn out equally and the wearing degree of the end surface of the respective optical fiber to be uniform for enhancing the yield rate during the end surfaces of the optical fibers being polished.

Figure 13:
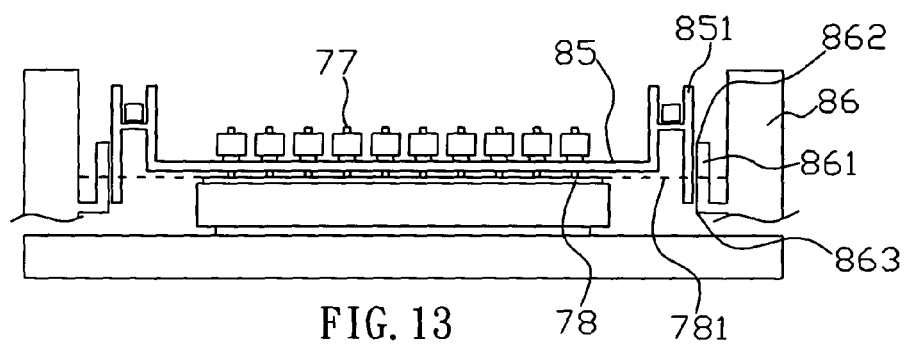
FIG. 13 is a fragmentary plan view of the sixth preferred embodiment of a polishing apparatus according to the present invention.

Please refer to FIG. 13 in company with FIG. 9. The sixth preferred embodiment of the holder according to the present invention comprises a main body 85 and a framework 86, and a structure thereof is approximately the same as the second embodiment shown in FIG. 9. The difference of the present embodiment is in that a lower end of a first supporting portion 851 is higher than a lower end of a second supporting portion 861, and an upper end of an inner wall of the second supporting portion 861 and a portion of the inner wall thereof corresponding to the lower end of the first supporting portion 851 are utilized to be the upper and lower contact portions 862, 863 respectively instead of the upper and lower contact portions 762, 763 disposed on the second supporting portion 761 of the second embodiment. The upper and lower contact portions 862, 863 are respectively positioned in a range approximately 2 centimeters above and below a contact plane 781 of the end surface of the respective optical fiber 77 with the polishing surface 78 to limit the angular movement of the first supporting portion 851. The present embodiment also provides a supporting structure for the main body to be manufactured easily and enable each polishing point of the polishing surface to be worn out equally and the wearing degree of the end surfaces of the optical fibers to be uniform for enhancing the yield rate during the end surfaces of the optical fibers being polished.

Figure 14:
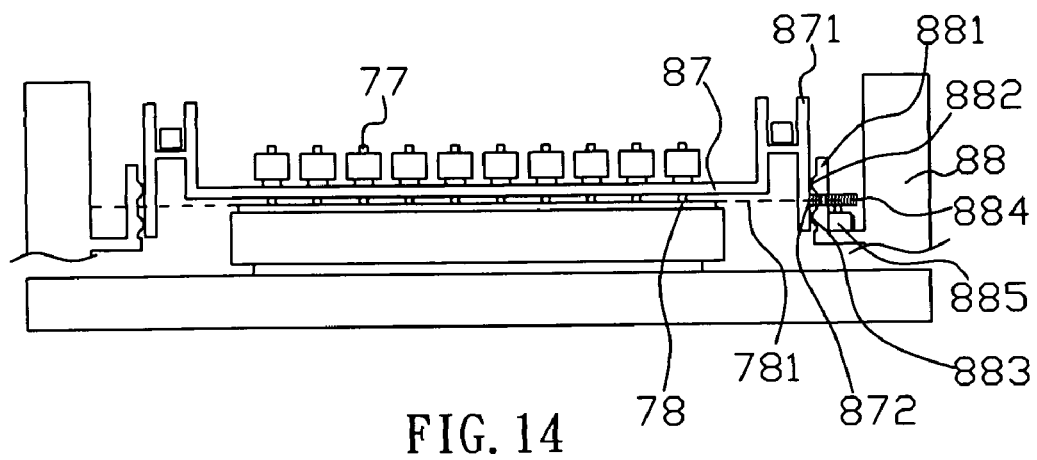
FIG. 14 is a fragmentary plan view of the seventh preferred embodiment of a polishing apparatus according to the present invention.

Please refer to FIG. 14 in company with FIG. 9. The seventh preferred embodiment of the holder according to the present invention comprises a main body 87 and a framework 88. A structure thereof is approximately the same as the second embodiment shown in FIG. 9. The difference of the present embodiment is in that the main body 87 and the framework 88 are not provided with the poker bar, long slot and breach as the main body 75 and the framework 76 of the second embodiment have. An outer wall of a first supporting portion 871 of the main body 87 is provided with a rack 872. A slot is disposed between first and second contact portions 882, 883 of the second supporting portion 881 of the framework 88. The framework is further coupled to a transmission mechanism 885. A transmission gear 884 of the transmission mechanism 885 passes through the slot of the second supporting portion 881. The main body 87 can be rotated by the transmission mechanism 885 when the rack 872 is engaged with the transmission gear 884. The upper and lower contact portions 882, 883 of the second supporting portion 881 can respectively limit the angular movement of the first supporting portion 871. The present embodiment also provides a supporting structure for the main body to be manufactured easily and enable each polishing point of the polishing surface to be worn out equally and the wearing degree of the end surfaces of the optical fibers to be uniform for enhancing the yield rate during the end surfaces of the optical fibers being polished. Besides, the main body 87 is driven to rotate with the transmission gear 884 to change the contact positions of the end surfaces of the optical fibers 77 on the polishing surface 78 for each polishing point of the polishing surface 78 to be brought into contact with the polished end surface of the corresponding optical fiber 77 uniformly such that each polishing point of the polishing surface 78 can be applied equally, the wearing degree thereof can be uniform, and the optical fibers 77 distributed at different positions can be polished identically for enhancing the yield rate during the end surfaces of the optical fibers 77 being polished.

Figure 15:
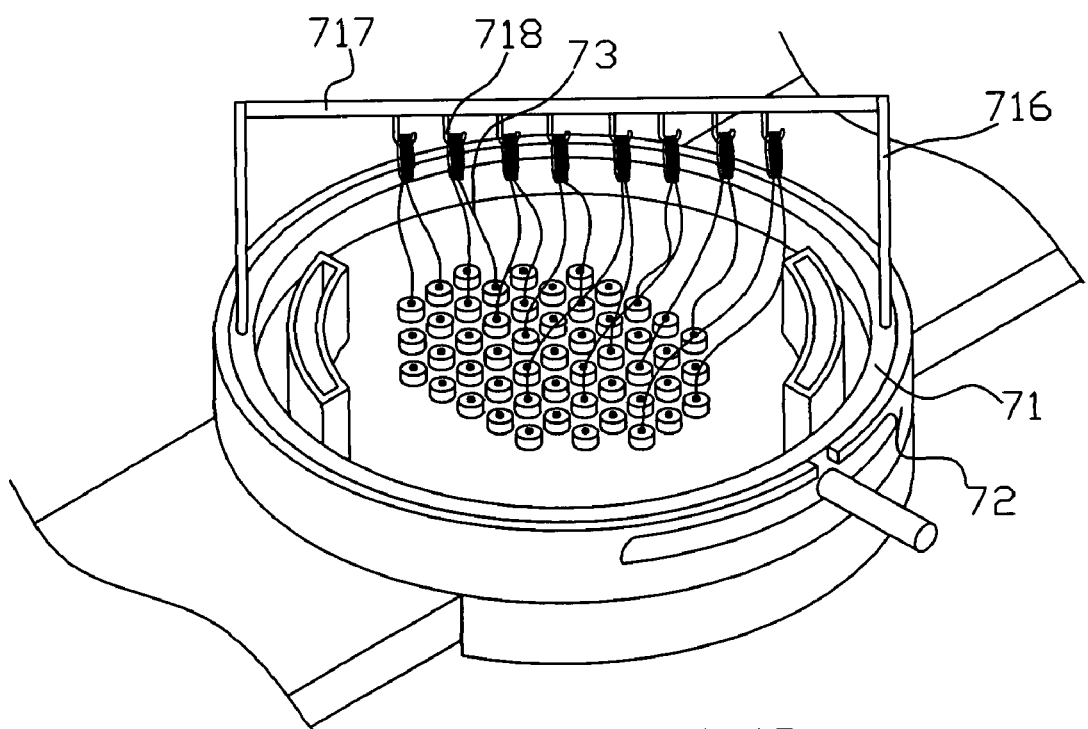
FIG. 15 is a perspective view of the eighth preferred embodiment of a polishing apparatus according to the present invention.

Please refer to FIG. 15 in company with FIGS. 7 and 8. The eighth preferred embodiment of the holder according to the present invention comprises the main body 71 and the framework 72 which are the same as those of the first embodiment. Besides, the main body 71 is further joined to a hanger 716 with a cross rod 717; the cross rod 717 is attached with a plurality of hooks 718. A middle section of the respective optical fiber 73 is coiled and then hung on the hooks 718. The present embodiment also provides a supporting structure for the main body to be manufactured easily to enable each polishing point of the polishing surface to be worn out equally and the wearing degree of each end surface of the respective optical fiber to be uniform for enhancing the yield rate during the end surfaces of the optical fibers being polished. Besides, each optical fiber 73 in the process of polishing can be arranged and fixed more conveniently with the hanger 716.

The second to seventh embodiments of the holder according to the present invention mentioned above may also be provided with the hanger 716 disclosed in the eighth embodiment for each optical fiber in the process of polishing can be conveniently arranged and fixed as well.

The first supporting portion of the main body disclosed in the present invention is ring-shaped instead of a plurality of fixing rods such that the production time and cost can be reduced greatly, and the difficult operation for adjusting the bottom ends of the fixing rods at the same level is unnecessary. The first supporting portion may be circular ring or other ring shapes.

The main body disclosed in the present invention can be rotated an angular movement relative to the framework and the polishing surface such that the contact position of the polished end surface of the respective optical fiber on the polishing surface can be changed for the polishing surface contacting with the polished end surface of the respective optical fiber uniformly with each polishing point of the polishing surface being applied evenly and the wearing degree thereof being uniform, and the optical fibers distributed at different positions can be polished identically for enhancing the yield rate during the end surfaces of the optical fibers being polished.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A polishing assembly comprising:
   a main body holder being provided with a plurality of fixtures to hold workpieces, and a ring-shaped first supporting portion at a periphery thereof;
   a framework having a second supporting portion surrounding an outer side of said first supporting portion to limit a movement of said first supporting portion to enable said main body holder to keep parallel to a polishing surface that is disposed inside a bottom of the second supporting portion;
   wherein said main body holder is further attached with a hanger which has a cross rod with multiple hooks for hanging the workpieces;
   wherein one of the first and second supporting portions is provided with an upper contact portion and a lower contact portion respectively above and below a contact plane of the end surface of the respective workpiece with said polishing surface.

2. The polishing assembly according to claim 1, wherein an inner wall of said second supporting portion is provided with said upper and lower contact portions.

3. The polishing assembly according to claim 1, wherein an outer wall of said first supporting portion is provided with said upper and lower contact portions.

4. The polishing assembly according to claim 1, wherein said second supporting portion is provided with a plurality of symmetrical screw holes to engage with a screw respectively; said screws project outward from an inner wall of said second supporting portion to form said upper and lower contact portions for spaces between said upper contact portion, said lower contact portion, and said first supporting portion being adjusted with said screws.

5. The polishing assembly according to claim 1, wherein a lower end of said first supporting portion is lower than a lower end of said second supporting portion, and upper and lower ends of an inner wall of said second supporting portion are said upper and lower contact portions respectively.

6. The polishing assembly according to claim 1, wherein a lower end of said first supporting portion is higher than a lower end of said second supporting portion; an upper end of an inner wall of said second supporting portion and a portion of an inner wall of said second supporting portion corresponding to the lower end of said first supporting portion are said upper and lower contact portions respectively.

7. The polishing assembly according to claim 1, wherein an outer wall of said first supporting portion is disposed with at least one poker bar; said second supporting portion is provided with a long slot for locating said poker bar such that said main body holder with the first supporting portion is capable of rotating relative to said framework and said polishing surface via the poker bar to change a contact position of the end surface of the respective workpiece on the polishing surface;
   wherein said second supporting portion is provided with a breach communicating with said long slot, and said poker bar passes through the breach and is located at said long slot.

8. The polishing assembly according to claim 7, wherein said second supporting portion is provided with a plurality of symmetrical screw holes to engage with a screw respectively; said screws project outward from an inner wall of said second supporting portion to form said upper and lower contact portions for spaces between said upper contact portion, said lower contact portion, and said first supporting portion being adjusted with said screws.

9. The polishing assembly according to claim 1, wherein an outer wall of said first supporting portion is provided with a rack; said second supporting portion is provided with a slot; said framework is further joined to a transmission mechanism; a transmission gear of said transmission mechanism is disposed at said slot to engage with the rack to rotate said main body holder so as to change a contact position of the end surface of the respective workpiece on the polishing surface.

10. The polishing assembly according to claim 9, wherein said second supporting portion is provided with a plurality of symmetrical screw holes to engage with a screw respectively; said screws project outward from an inner wall of said second supporting portion to form said upper and lower contact portions for spaces between said first contact portion, said second contact portion, and said first supporting portion being adjusted with said screws.

* * * * *